United States Patent [19]

Cooker et al.

[11] Patent Number: 5,041,677

[45] Date of Patent: Aug. 20, 1991

[54] PROCESS FOR SYNTHESIZING 4,4'-DIHYDROXYDIPHENYL SULFONE

[75] Inventors: Bernard Cooker, Piscataway; Fred Zemlanicky, Hillside, both of N.J.

[73] Assignee: Amoco Corporation, Chicago, Ill.

[21] Appl. No.: 500,752

[22] Filed: Mar. 28, 1990

Related U.S. Application Data

[63] Continuation of Ser. No. 359,534, Jun. 1, 1989, abandoned, which is a continuation of Ser. No. 904,804, Sep. 8, 1986, abandoned, which is a continuation of Ser. No. 784,045, Oct. 4, 1985, abandoned.

[51] Int. Cl.$^5$ .......................................... C07C 315/04
[52] U.S. Cl. ..................................................... 568/33
[58] Field of Search ........................................ 568/33

[56] References Cited

U.S. PATENT DOCUMENTS

| | | | |
|---|---|---|---|
| 3,065,274 | 11/1962 | Vegter et al. | 568/33 |
| 3,297,766 | 1/1967 | Bradley et al. | 568/33 |
| 3,366,692 | 1/1968 | Orem | 568/33 |
| 4,162,270 | 7/1979 | Ogata et al. | 568/33 |
| 4,382,147 | 5/1983 | Kitamura et al. | 568/33 |

FOREIGN PATENT DOCUMENTS

| | | | |
|---|---|---|---|
| 165526 | 2/1953 | Australia | 568/33 |
| 50-116446 | 9/1975 | Japan | 568/33 |
| 2030566 | 4/1980 | United Kingdom | 568/33 |

OTHER PUBLICATIONS

Hinkel et al., Chem. Society Journal (1949), p. 2854.

*Primary Examiner*—Mary E. Ceperley
*Attorney, Agent, or Firm*—Frederick S. Jerome; William H. Magidson; Ralph C. Medhurst

[57] ABSTRACT

Process for synthesizing 4,4' bisphenol sulfone involving reacting phenol and sulfuric acid in an inert reaction solvent, and maintaining the reaction solvent at temperatures of about 160 to 200° C. and at a predetermined level sufficient to maintain a saturated 4,4' isomer solution and an unsaturated 2,4' isomer solution, thereby selectively yielding 4,4' bisphenol sulfone with minimal amounts of 2,4' isomer by-product.

5 Claims, No Drawings

PROCESS FOR SYNTHESIZING 4,4'-DIHYDROXYDIPHENYL SULFONE

This is a continuation of application Ser. No. 07/359,534, filed June 1, 1989 which is a continuation of Ser. No. 06/904,804, filed Sept. 8, 1986, which in turn is a continuation of Ser. No. 06/784,045, filed Oct. 4, 1985, all abandoned.

FIELD OF THE INVENTION

This invention relates to a process for synthesizing 4,4' dihydroxydiphenyl sulfone. More particularly, this invention relates to a process for synthesizing and recovering 4,4' bisphenol sulfone from phenol and sulfuric acid.

BACKGROUND OF THE INVENTION

It is known that 4,4' bisphenol sulfone (4,4' dihydroxydiphenyl sulfone) can be synthesized from phenol and sulfuric acid by reactions that may be depicted by the following equations:

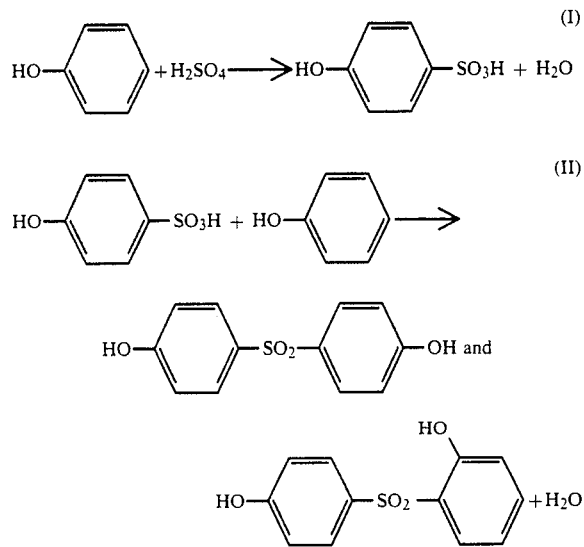

The end product of the reactions is a mixture of the 4,4' and 2,4' isomers of bisphenol sulfone. As these favored reactions proceed, there occur also side reactions which produce small amounts of quinone-type coloring agents and other impurities which have not been fully identified.

The formation of both 2,4' bisphenol sulfone by-product and side-product impurities is apparently inevitable and is certainly undesirable. Not only does their formation reduce the yield of the 4,4' bisphenol sulfone, but also the presence of these products greatly reduces the utility of the recovered bisphenol sulfone product. A particularly useful application of 4,4' bisphenol sulfone is as a monomer in the production of high molecular weight polymers such as polyphenylsulfone resins. However, to be maximally useful in such polymerizations, 4,4' bisphenol sulfone must be substantially free of its 2,4' isomer and otherwise be of high purity. Polymers made from 4,4' bisphenol sulfone having a significant amount of 2,4' isomer generally neither reach the high molecular weights nor exhibit the good temperature resistance and mechanical properties that are common to polymers made from purer 4,4' bisphenol sulfone. Accordingly, it is most desirable for a commercial process that formation of 2,4' bisphenol sulfone and other impurities be minimized in the synthesis of 4,4' bisphenol sulfone.

One technique that has been proposed for increasing the yield of 4,4' bisphenol sulfone involves distilling from the reaction medium the water formed in the reactions of phenol with sulfuric acid (Australian Patent No. 165,526). Entraining the evolved water in a solvent has also been proposed (e.g. U.S. Pat. No. 3,065,275). The removal of water by either of these methods results in a forward equilibrium shift in the reactions, depicted by equations I and II above, thereby increasing the production of 4,4' bisphenol sulfone. However, simply altering the equilibrium of the reactions between phenol and sulfuric acid also proportionately increases the production of undesirable 2,4' bisphenol sulfone by-product.

It is known that, in the liquid phase, the 4,4' and 2,4' isomers of bisphenol sulfone exist in a dynamic equilibrium which may be depicted by the following equation:

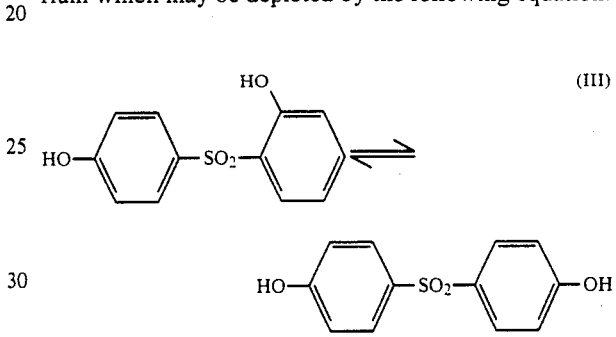

Removal of 4,4' bisphenol sulfone from the liquid phase results in a forward shift in the dynamic equilibrium, with the 2,4' isomer rearranging to the 4,4' isomer to reestablish the equilibrium concentrations. In other words, by removing 4,4' bisphenol sulfone from the liquid phase, the amount of 2,4' isomer by-product can be decreased while the production of the desired 4,4' bisphenol sulfone is increased.

One method that has been proposed to increase the yield of 4,4' bisphenol sulfone, by taking advantage of the liquid phase equilibrium, is described in U.S. Pat. No. 3,297,766. The described method involves precipitating 4,4' bisphenol sulfone from a conventionally formed isomer mixture, then recycling the remainder of the mixture to the reaction medium, with additional sulfuric acid and phenol reactants, whereupon some of the returned 2,4' isomer is said to rearrange to 4,4' bisphenol sulfone. This method, however, does not achieve satisfactorily high yields of 4,4' bisphenol sulfone until after the recycle is repeated several times.

Another method that is said to produce 4,4' bisphenol sulfone in high yield with minimal amounts of 2,4' isomer is described in U.S. Pat. No. 4,162,270. The described process involves reacting phenol with sulfuric acid in the presence of a solvent which is progressively removed from the reaction medium as the reaction proceeds. Removal of the solvent, it is said, causes the produced 4,4' bisphenol sulfone to precipitate and 2,4' isomer to rearrange to 4,4' bisphenol sulfone to reestablish the liquid phase equilibrium. The proposed method requires the complete removal of the solvent by vacuum distillation. Accordingly, this method is unattractive due to the expense and inconvenience of using vacuum and additional distillation equipment. The method is also cumbersome in requiring the use of a second solvent feed to recover from the reactor the precipitated product which may be an almost intractable solid mass.

Yet another proposed method for effecting rearrangement of 2,4' bisphenol sulfone by-product to the desired 4,4' bisphenol sulfone is described in United Kingdom Patent Application No. 2,030,566. In the described method, after a crystallized isomer mixture of bisphenol sulfone is formed, it is dissolved in an organic solvent and heated with an acidic catalyst to cause isomer rearrangement. This two step method of synthesizing higher proportions of 4,4' bisphenol sulfone, however, is inefficient due to the prolonged periods of heating and the possible production of additional side reaction impurities during the catalyzed isomer rearrangement step.

SUMMARY OF THE INVENTION

This invention relates to a process for synthesizing 4,4' bisphenol sulfone, which process comprises reacting phenol and sulfuric acid at an elevated temperature in an inert reaction solvent to form a reaction product mixture comprising 4,4' bisphenol sulfone and 2,4' bisphenol sulfone; and maintaining the temperature of the reaction product mixture at about 160° to about 200° C. while simultaneously maintaining the inert reaction solvent at a predetermined level. The predetermined level of solvent is sufficient to maintain in the reaction product mixture a saturated 4,4' bisphenol sulfone solution and an unsaturated 2,4' bisphenol sulfone solution, whereby 4,4' bisphenol sulfone selectively crystallizes from the reaction product mixture.

In one embodiment of this invention, recovery of the thus synthesized 4,4' bisphenol sulfone comprises, subsequent to maintaining the temperature at about 160° to about 200° C., reducing the temperature of the reaction product mixture sufficient to selectively crystallize additional 4,4' bisphenol sulfone from the reaction product mixture.

Simultaneously with, or subsequent to, reducing the temperature, the recovery process may further comprise adding additional inert reaction solvent to the reaction product mixture whereby the total amount of inert reaction solvent is sufficient to substantially maintain the 2,4' bisphenol sulfone in solution at the reduced temperature.

By maintaining a minimum amount of reaction solvent at a temperature from about 160° to about 200° C. in accordance with the present invention, it is thought that a liquid phase in the reaction solvent is established in which the reactants dissolve and the synthesis proceeds. Thus, at temperatures above about 160° C. the reaction between phenol and sulfuric acid forms bisphenol sulfone in the reaction solvent in an isomer ratio satisfying the liquid phase equilibrium. Apparently, the equilibrium ratio of 4,4' to 2,4' isomer formation in the liquid phase is normally about 3:1. However, the reaction solvent is maintained at a limited level in the synthesis of this invention such that the saturation point of the 4,4' bisphenol sulfone isomer in the reaction solvent will be exceeded while the liquid phase is present. At this point, 4,4' bisphenol sulfone crystallizes from the reaction solvent, momentarily leaving the liquid phase no longer at equilibrium. To reestablish equilibrium, the newly forming bisphenol sulfone arranges in the 4,4' isomer structure. Hence, 2,4' isomer formation is suppressed and 4,4' bisphenol sulfone production is enhanced.

In addition, any 2,4' isomer that formed prior to establishing the liquid phase in the reaction solvent, is thought to enter the liquid phase on its establishment in the reaction solvent. The disproportionate 2,4' isomer concentration then results in the 2,4' isomer rearranging to the 4,4' isomer structure in order to maintain the liquid phase equilibrium. Again, once the reaction solvent is saturated with the 4,4' isomer, 4,4' bisphenol sulfone crystallizes from the reaction product mixture. Thus, even after completion of the reaction between phenol and sulfuric acid, continued maintenance of a liquid phase in the reaction solvent can enhance the yields of 4,4' bisphenol sulfone.

Further high yields of 4,4' bisphenol sulfone are recoverable from the synthesis by reducing the temperature of the reaction product mixture to crystallize additional 4,4' bisphenol sulfone. By one embodiment of this invention, the 4,4' bisphenol sulfone is recovered in high purity by adding additional reaction solvent during, or subsequent to, this cooling. The addition of reaction solvent tends to keep the already solvated 2,4' isomer in solution at the reduced temperature. Thus the 4,4' isomer is recovered with minimal amounts of 2,4' isomer impurity.

The synthesis process of the present invention produces, in a single cycle, high yields of bisphenol sulfone having an enhanced 4,4' to 2,4' isomer ratio. The synthesized 4,4' bisphenol sulfone is readily recoverable from the reaction in the same solvent employed in the synthesis and with minimal 2,4' bisphenol sulfone and other impurities. Accordingly, the inventive process is most attractive for commercial operations.

DETAILED DESCRIPTION OF THE INVENTION 4,4' bisphenol sulfone of high purity is obtained in high yields by the synthesis process according to the present invention. The present invention involves the following. Phenol and sulfuric acid are reacted in an inert reaction solvent to form a reaction product mixture. The mixture consists of a solid phase comprising 4,4' bisphenol sulfone and a liquid phase comprising 4,4' bisphenol sulfone and 2,4' bisphenol sulfone dissolved in the solvent. The temperature of the reaction product mixture is maintained at a temperature from about 160° to about 200° C., while the level of inert reaction solvent is simultaneously maintained such that the reaction product mixture is saturated with 4,4' bisphenol sulfone but unsaturated with 2,4' bisphenol sulfone. Under these conditions of temperature and solvent quantity, 4,4' bisphenol sulfone crystallizes from the reaction product mixture. To recover the 4,4' bisphenol sulfone, the reaction product mixture then is cooled to selectively crystallize additional 4,4' bisphenol sulfone from the product mixture, and additional solvent is added as necessary to substantially maintain the 2,4' bisphenol sulfone dissolved in the solvent.

Achievement of enhanced yields and purity of the 4,4' bisphenol sulfone by the process of this invention is directly dependent on maintaining a specific level of reaction solvent during synthesis; and also during recovery.

During the synthesis of 4,4' bisphenol sulfone from phenol and sulfuric acid, when the temperature of the reaction product mixture is at about 160° to 200° C., the reaction solvent is maintained at a level sufficient to solubilize the phenol and sulfuric acid reactants, the phenol sulfonic acid intermediate reactant, and the 2,4' bisphenol sulfone by-product. The level of solvent, however, is limited here in the synthesis to a quantity less than sufficient to solubilize all of the formed 4,4' bisphenol sulfone. Maintaining the level of reaction solvent within this range throughout the period at which the temperature is above 160° C. has been found to suppress the formation of the 2,4' isomer of bisphenol sulfone and enhance the formation of the desired 4,4' bisphenol sulfone.

Within limits, the lesser the amount of reaction solvent present, the greater is the proportion of the 4,4' bisphenol sulfone isomer to 2,4' isomer produced. As stated previously, at minimum the amount of solvent present is sufficient to dissolve the reactants and solvate an initial amount of the bisphenol sulfone product so that the synthesis, at least in part, will proceed in a solvent-liquid phase. At maximum the amount of solvent maintained, while the temperature of the synthesis is above about 160° C., is less than sufficient to solubilize all of the bisphenol sulfone being formed. In addition to these limits, practical considerations dictate that in a commercial operation the solvent be present in an amount sufficient to prevent the crystallized 4,4' bisphenol sulfone from becoming a solid mass trapped in the reactor vessel. Accordingly, it is preferred that the solvent be maintained during synthesis in such an amount that the resulting reaction product mixture will comprise from about 15 to about 35 weight percent solvent; and more preferably from about 20 to about 25 weight percent solvent.

During the recovery of the 4,4' bisphenol sulfone from the reaction product mixture, the amount of solvent present is a quantity sufficient to solubilize at least a majority of the 2,4' bisphenol sulfone by-product. In other words, the amount of reaction solvent should be sufficient to maintain the already solvated 2,4' bisphenol sulfone isomer by-product as fully in solution as practical while the product mixture is cooled and the desired 4,4' bisphenol sulfone is removed from the reaction product mixture. The employment of at least that amount of solvent results in recovered 4,4' bisphenol sulfone with minimal amounts of 2,4' isomer impurity. On the other hand, unduly large amounts of solvent will dissolve appreciable amounts of the 4,4' bisphenol sulfone product resulting in lower yields of recovery. Further, commercial considerations direct that the solvent be employed in a quantity that enables the 4,4' bisphenol sulfone to be easily and efficiently removed from the reaction product mixture by filtration, centrifugation or similar means.

Based on these considerations, it has been found that for maximum recovery of 4,4' bisphenol sulfone with minimal 2,4' isomer by-product, the reaction solvent normally should be present during recovery in such an amount that the resulting reaction product mixture will comprise from about 20 to about 80 weight percent solvent. Preferably, the 4,4' bisphenol sulfone suspension will comprise from about 25 to about 50 weight percent solvent at the recovery stage of the present invention.

Of course, where after completion of the synthesis the reaction solvent is present in the reaction product mixture in an amount less than that desired for recovery, additional solvent is added either prior to, or preferably, simultaneously with the cooling of the reaction product mixture.

The reaction solvents employed in the process of this invention are inert under the conditions of the process. The solvents dissolve phenol, sulfuric acid, phenol sulfonic acid and, to a limited extent, bisphenol sulfone; and have boiling points sufficiently high that they do not rapidly vaporize from the reaction mixture at the elevated temperatures of the synthesis. Preferred inert solvents are those which are more effective in solvating the 2,4' isomer of bisphenol sulfone than the 4,4' isomer. The use of such inert solvents maximizes the yield and purity of 4,4' bisphenol sulfone by keeping the 2,4' isomer solvated throughout the process, while the 4,4' bisphenol sulfone readily crystallizes therefrom during synthesis and recovery. Examples of suitable reaction solvents include branched and straight-chain alkanes such as nonane, heptane, tetrachloroethane, trichloroethane, dichloroethane, substituted aromatics such as dichlorobenzene, trichlorobenzene, mixtures thereof, and the like. Dichlorobenzene and trichlorobenzene are preferred reaction solvents.

In the process of this invention, 4,4' bisphenol sulfone is synthesized from phenol and sulfuric acid in an inert reaction solvent at temperatures normally from about 160° to 200° C. As phenol and sulfuric acid will react efficiently at temperatures as low as about 110° C. to form bisphenol sulfone, it is not necessary that at the commencement of the synthesis the reaction be at a higher temperature. However, the temperature must be raised eventually to achieve enhanced yields of 4,4' bisphenol sulfone in accordance with the principles of the present invention.

The temperature of the reaction product mixture normally must exceed about 160° C. to obtain an appreciable bisphenol sulfone liquid phase. As set forth above, the presence of a bisphenol sulfone liquid phase with solvent promotes the preferential formation of 4,4' bisphenol sulfone. The temperature of the reaction product mixture generally is maintained below about 200° C. because at higher temperatures significant amounts of quinone-type coloring agents and other side-reaction products might be produced. Therefore, the temperature of the reaction product mixture is maintained during the process of this invention in the range from about 160° to about 200° C.; preferably from about 180° to about 190° C.

At the temperatures of the synthesis, the water evolved in the reactions between phenol and sulfuric acid will vaporize along with a portion of the phenol and a portion of the reaction solvent. Therefore, an azeotrope of water and phenol is removed from the reaction medium during the course of the synthesis by, for example, distillation and condensation. Removal of water in the process of this invention depresses its concentration in the reaction product mixture, thereby driving the favored reactions forward to the formation of 4,4' bisphenol sulfone.

As a portion of the inert reaction solvent also vaporizes at the reaction temperatures, the condensate of the removed vapors comprises two layers: an aqueous layer comprising phenol and water and an organic layer comprising phenol and solvent. The two layers can be readily separated by decanting or similar means. The solvent layer then may be returned to replenish the reaction solvent content of the reaction product mixture as necessary to maintain the minimum desired solvent concentration. Of course, fresh solvent also may be fed to the reaction product mixture to replace the vaporized solvent.

Phenol and sulfuric acid are employed in the process of this invention in molar ratios from slightly less than to greater than the stochiometric ratio of 2 to 1. As phenol is partly vaporized and removed during the course of the reaction, it may be desirable to employ phenol in excess of the stochiometric amount required. Satisfactorily maximized yields of bisphenol sulfone are obtained with an 0.3 mole excess of phenol, but an excess of at least 0.5 mole of phenol is generally required to produce the greatest yield. However, it has been found that the use of less than the stochiometric 2 moles of phenol results in preferential formation of the 4,4' bisphenol sulfone isomer. Accordingly, it is preferred that slightly less phenol than 2 moles (not including the amount of phenol lost to the reaction medium by vaporization) be reacted per mole of sulfuric acid. From about 1.9 to 1.99 moles of phenol per mole of sulfuric acid is most preferred.

The phenol and sulfuric acid may be mixed together in the inert reaction solvent by adding one with or to the other either continuously, incrementally, or all at once so as to achieve the reaction. Thus the reaction readily can be conducted in batch, semi-continuous, or continuous operation by the proper selection or adjustment of addition rates, reaction rate and temperature as is conventional to control the reaction exotherm.

However, it has been found that the quinone-type coloring agents and other impurities are formed in lesser quantities in the reaction solvent of this invention when the acid concentration is kept low. Therefore, it is desirable in the process of the present invention to slowly feed the sulfuric acid into the reaction solvent over the course of the reaction at about the rate the sulfuric acid is consumed. A preferred method is to combine the phenol with the solvent, heat the mixture to about 130° C., then add the sulfuric over a period of time of about one hour. As the sulfuric acid is added, the temperature of the reaction product mixture will increase due to the reaction exotherm, and additional heat is supplied to raise the temperature of the reaction product mixture to about 160° to 200° C.

The reaction between the phenol and sulfuric acid proceeds for a period of time sufficient to effect maximum conversion of the reactants to bisphenol sulfone. Generally, about 1 to 5 hours are sufficient.

As previously stated, the temperature of the reaction product mixture need not be maintained at about 160° to 200° C. throughout the reaction. Maintenance of the reaction product mixture at temperatures of about 160° to 200° C. during only the later portion of the reaction is sufficient to achieve enhanced formation of 4,4' bisphenol sulfone. However, when the temperature of the reaction product mixture is not maintained at about 160° to 200° C. for a major portion of the reaction, it is preferred that the temperature be so maintained for a sufficient period of time after completion of the reaction to effect rearrangement of 2,4' isomer to 4,4' bisphenol sulfone. Generally, maintaining the reaction product mixture at about 160° to 200° C. for about one-half to about 3 hours after completion of the reaction is sufficient.

During the synthesis, the reaction medium should be agitated moderately to aid the distillation removal of the evolved water and to maintain the crystals of 4,4' bisphenol sulfone in suspension. Suitable agitators include a 2 blade anchor, a 4 blade pitch batch turbine, and the like.

When the synthesis is completed, the resulting reaction product mixture is preferably cooled, and additional solvent added if needed or desired, to selectively crystallize additional 4,4' bisphenol sulfone. While it is possible to recover 4,4' bisphenol sulfone from the reaction product mixture at or near the 160° to 200° C. temperature of the synthesis by hot filtration or similar means, such recovery is not practical. Recovery at such elevated temperatures would recover only the 4,4' bisphenol sulfone that has crystallized from the reaction product mixture during the synthesis and perhaps a small portion that was dissolved in the solvent. Hot filtration is also not attractive because of the handling and material problems normally attendent with such high temperature procedures.

Therefore, in the process of this invention, after completion of the synthesis of 4,4' bisphenol sulfone, the reaction product mixture is preferably cooled to a reduced temperature thereby selectively crystallizing additional 4,4' bisphenol sulfone. Though temperatures to ambient may be used in the recovery of 4,4' bisphenol sulfone, such low temperatures may substantially hamper the recovery of 4,4' bisphenol sulfone, by filtration or centrifugation, due to the accompanying increase in the viscosity of the reaction product mixture. Therefore, the reduced temperature to which the reaction product mixture is cooled is normally from about 80° to about 120° C. These temperatures are generally sufficiently high to maintain substantial solvation of the 2,4' bisphenol sulfone by-product and other impurities in the solvent, yet are low enough that 4,4' bisphenol sulfone readily crystallizes from the reaction product mixture in high yield.

The crystallized 4,4' bisphenol sulfone is then separated from the reaction product mixture by vacuum filtration, pressure filtration, centrifugation or similar means. The collected crystals of 4,4' bisphenol sulfone are preferably washed with additional solvent to remove traces of liquor and impurities that may have collected on the crystals' surfaces. Though solvent at ambient temperature to its boiling point may be used in the wash, it is preferred that the solvent be at a temperature from about 50° to about 120° C. Solvent at lower temperatures may possibly cause some 2,4' bisphenol sulfone in the liquor on the crystals to precipitate, while a higher temperature wash might dissolve and wash away some of the 4,4' bisphenol sulfone crystals.

Typical yields of 4,4' bisphenol sulfone from the process of this invention are at least 75 percent of theoretical based on total conversion of the sulfuric acid. The recovered 4,4' bisphenol sulfone is also of high purity, typically at least 93 percent pure.

As the solvents employed are inert under the synthesis conditions of the process, a recycle may be employed in the practice of this invention. In the recycle, the mother liquor from the recovery is recycled for use in a subsequent synthesis. The wash liquor also can be recycle. These liquors consist principally of solvent, phenol, unrecovered 4,4' bisphenol sulfone, 2,4' bisphenol sulfone by-product, and other impurities. When the liquor is added to a reaction medium, with additional quantities of sulfuric acid and phenol, and the temperature is maintained above about 160° C., 2,4' bisphenol sulfone isomer in the liquor rearranges to 4,4' isomer in the following synthesis in accordance with the equilibrium equation III set forth above, thus enhancing the yield of 4,4' bisphenol sulfone.

A preferred embodiment of the process of the present invention involves initially charging a reactor with commercial grade ortho-dichlorobenzene as the reaction solvent in an amount such that the resulting reaction product mixture will comprise about 25 weight percent solvent. Phenol and sulfuric acid are continuously fed to the reactor at a molar ratio of about 1.98 to 1. The reactor is operated at about 185° C. and the reaction product mixture is agitated by an anchor stirrer or a high velocity pumped external circulation loop. Water formed in the synthesis is distilled continuously from the reactor along with a portion of the orthodichlorobenzene and phenol. The vapor is condensed and the solvent layer is recycled to the reactor. At completion of the reaction, the reaction product mixture is flushed from the reactor and transferred to a vacuum crystallizer where the reaction product mixture is cooled to a temperature of about 120° C. The slurry from the crystallizer is then fed to a centrifuge where the crystallized product is separated from the liquor and then washed with additional dichlorobenzene at about 90° C. A portion of the liquor from the centrifuge, which is a combination of reactor and wash liquors, is then recycled to the reactor.

The following examples are provided to illustrate the present invention. The examples are not to be construed as limiting the invention as it will be readily apparent to one skilled in the art that various modifications can be made in the examples in accordance with the principles of the present invention.

EXAMPLE I

Ortho-dichlorobenzene (42.7 gm) and phenol (96.1 gm) were charged to a 500 ml round bottom flask and purged with nitrogen for 15 minutes at 40° C. The flask was heated in an oil bath and was fitted with a Teflon paddle stirrer and two thermometers with bulbs in the liquid and the vapor.

The temperature of the mixture of phenol and ortho-dichlorobenzene (O-DCB) in the reactor was raised to 130° C. over 70 minutes. Then 49.6 gm of 96% (wt) sulfuric acid were added to the flask over 55 minutes. During this time the mixture changed in color from colorless to dark pink and the temperature rose from 130° C. to 154° C. due to the reaction exotherm. Over 95 minutes the temperature was increased to 188° C. The vapor from the flask flowed to a water-cooled condenser. The condensate flowed into a Dean-Stark trap where water with dissolved phenol and O-DCB containing dissolved phenol separated into two layers with the aqueous layer uppermost. Fresh O-DCB was added to the reactor in the same amount as the O-DCB in the lower layers of the condensate. No further water evolved after this time. The volume of the aqueous layer was 18 ml, indicating essentially complete reaction (the theoretical volume of water, based on complete conversion of the sulfuric acid to bisphenol sulfone, was 19 ml). The inventory of O-DCB in the reactor was approximately 42 gm. A slight cloudiness developed at 188° C., indicating crystallization of products from the reaction mixture.

Over the following 50 minutes, 445 gm of O-DCB were added to the reaction flask to reduce the reactor temperature from 188° C. to 134° C. Products precipitated during this time. Further precipitation occurred as the mixture was cooled with agitation to 80° C. The entire reactor content was vacuum filtered at 80° C. using a Buchner funnel and paper. The filter cake was washed with 129.8 gm O-DCB and then with methylene chloride.

One hundred and six grams of wet cake were collected. This material was analyzed by liquid chromatography and the composition of the bisphenol sulfone content of the wet cake was determined to comprise 93.5 weight percent 4,4'bispenol sulfone and 6.5 weight percent 2,4'bispenol sulfone. The by-products present could not be detected by the liquid chromatography technique. The cake was assumed to be 93% bisphenol sulfone and 7% O-DCB by weight. Accordingly, the 4,4'bisphenol sulfone yield was 76% of the theoretical yield of 121.5 gm (based on complete conversion of the sulfuric acid).

EXAMPLE II

Orthodichlorobenzene (87.9 gm) and phenol (184.8 gm) were charged to a 1000 ml round bottom flask. The flask was heated in an oil bath and was fitted with a Teflon paddle stirrer and a thermometer with its bulb in the liquid.

The temperature of the mixture of phenol and ortho-dichlorobenzene (O-DCB) in the reactor was raised to 130° C. over 1 hour while purging with nitrogen. Then 100.3 gm of 96% (wt) sulfuric acid were added to the flask over 60 minutes. The molar ratio of phenol to sulfuric acid was 2.0:1. During this time the mixture changed in color from clear colorless to dark pink and the temperature rose from 130° C. to 153° C. due to the reaction exotherm. Distillation commenced at 147° C. The vapor from the flask flowed to a water-cooled condenser. The condensate flowed into a Dean-Stark trap where water with dissolved phenol and O-DCB containing dissolved phenol separated into two layers, the aqueous layer being uppermost. The O-DCB inventory in the reactor was maintained by recycling the lower layer from the trap. Over the following 60 minutes the temperature increased to 180° C. The aqueous layer in the trap was 39 ml in volume on reaching 180° C. in the reactor. The theoretical volume of water for complete conversion was 39.5 ml. During the next 95 minutes the temperature rose to 185° C. and light-colored crystals were seen precipitating in the reactor. The reactor was cooled to ambient temperature over 1 hour.

The following day the reaction mixture was reheated to 180° C. over 80 minutes and reaction continued for 60 further minutes while the temperature increased to 185° C. The precipitation which was observed the previous day continued but did not exceed 10 to 15% by volume of the reactor contents. All O-DCB condensate was recycled.

Nine hundred and six grams of O-DCB were added to the material over 15 minutes, cooling the mixture to 120° C. This yielded a dark pink slurry of crystals and liquor which was kept mobile by the agitator. The crystals were 15 to 20% of the reactor volume and were in the form of needles up to ¼ inch in length. A sintered glass filter funnel was used to vacuum filter the crystals from the liquor at 120° C. The filter cake was washed with 391.5 gm of O-DCB at 120° C., followed by 391.5 gm of O-DCB at 25° C. 228.5 grams of wet, washed cake were collected.

The composition of the bisphenol sulfone content of the cake, as determined by gas chromatography, was 95.3 weight percent 4,4'bisphenol sulfone and 4.7 weight percent 2,4'bisphenol sulfone. The by-products present could not be detected by the gas chromatograph technique employed. The cake was assumed to be 93% bisphenol sulfone and 7% orthodichlorobenzene. The 4,4'bisphenol sulfone yield was, therefore, 82% of the theoretical yield of 245.7 gm (based on the amount of sulfuric acid employed).

What is claimed is:

1. A process for synthesizing 4,4'-bisphenol sulfone which comprises reacting phenol and sulfuric acid in an inert reaction solvent selected from the group consisting of dichlorobenzene, trichlorobenzene and mixtures thereof, said solvent comprising about 15 to about 35 weight percent of the reaction mixture, to form a reaction product mixture comprising 4,4'-bisphenol sulfone and 2,4'-bisphenol sulfone, and removing water of reaction between phenol and sulfuric acid at a temperature of about 160° to about 200° C., maintaining the temperature of the reaction product mixture at about 160° to about 200° C. until after there is no further water evolved from the reaction, cooling the product mixture to about 80° to about 120° C., adding an additional amount of the inert solvent, if necessary, to form a slurry comprising from about 20 to 80 weight percent of the inert solvent and partitioning said slurry to obtain crystalline 4,4'-bisphenol sulfone and liquor containing dissolved therein 2,4'-bisphenol sulfone.

2. The process of claim 1 further comprising adding additional inert reaction solvent to the reaction product mixture simultaneously with or subsequent to reducing the temperature; whereby the total amount of inert reaction solvent is sufficient to substantially maintain the 2,4'bisphenol sulfone in solution at the reduced temperature.

3. The process of claim 2 wherein the total amount of inert reaction solvent at the reduced temperature is from about 25 to about 50 weight percent of the reaction product mixture.

4. The process of claim 1 wherein less than 2 moles of phenol are reacted per mole of sulfuric acid.

5. The process of claim 4 wherein from about 1.9 to about 1.99 moles of phenol are reacted per mole of sulfuric acid.

* * * * *